United States Patent [19]

Chen et al.

[11] Patent Number: 5,670,057

[45] Date of Patent: Sep. 23, 1997

[54] APPARATUS AND METHOD FOR AUTOMATICALLY PERFORMING PERITONEAL EQUILIBRATION TESTS

[75] Inventors: Chi Chen, Hawthorn Woods, Ill.; Paul Emerson, St. Louis Park; Prakash Keshaviah, Plymouth, both of Minn.

[73] Assignee: Baxter International Inc., Deerfield, Ill.

[21] Appl. No.: 434,302

[22] Filed: Apr. 28, 1995

[51] Int. Cl.[6] ................................................. A61M 1/28
[52] U.S. Cl. .................... 210/739; 210/85; 210/86; 210/97; 210/252; 210/646; 604/29
[58] Field of Search .......................... 210/645, 646, 210/647, 739, 929, 85, 86, 97, 252; 604/28, 29, 30, 65; 364/413.01, 413.02

[56] References Cited

U.S. PATENT DOCUMENTS

| | | | |
|---|---|---|---|
| 4,096,859 | 6/1978 | Agarwal et al. | 210/929 |
| 4,348,283 | 9/1982 | Ash | 210/321.67 |
| 4,560,472 | 12/1985 | Granzow et al. | 604/29 |
| 5,004,459 | 4/1991 | Peabody et al. | 604/29 |
| 5,110,477 | 5/1992 | Howard et al. | 210/647 |
| 5,141,492 | 8/1992 | Dadson et al. | 604/29 |
| 5,308,315 | 5/1994 | Khuri et al. | 604/4 |
| 5,324,422 | 6/1994 | Colleran et al. | 210/85 |
| 5,401,238 | 3/1995 | Pirazzoli | 604/4 |
| 5,445,610 | 8/1995 | Evert | 604/29 |
| 5,518,623 | 5/1996 | Keshaviah et al. | 210/646 |

FOREIGN PATENT DOCUMENTS

| | | |
|---|---|---|
| 0 495 412 A1 | 7/1992 | European Pat. Off. |
| 4-166166 | 12/1992 | Japan. |

OTHER PUBLICATIONS

"Membrane Phenomena and Mass Transfer Kinetics in Peritoneal Dialysis" in the *Journal of Membrane Science* by Michael J. Lysaght and Peter C. Farrell, vol. 44, pp. 5–33 (1989).

*Primary Examiner*—John Kim
*Attorney, Agent, or Firm*—Thomas S. Borecki; Charles R. Mattenson; Anibal Jose Cortina

[57] ABSTRACT

There is disclosed a method and apparatus for automatically conducting peritoneal equilibration testing. The method involves removing a sample of overnight dwell fluid from a patient in an amount sufficient to determine the concentration of a metabolite in the drain fluid. The concentration of the metabolite in the sample is then detected and the overnight dwell fluid is drained and weighed. A known weight of dialysate fluid is instilled into a patient and thereafter there are periodically withdrawn samples of the dialysate fluid and the concentration of metabolite in each sample is determined. The ratio of metabolite concentration of each of the periodically drawn samples to metabolite concentration for the overnight dwell fluid is determined. The patient is then drained after a predetermined dwell time and the volume of drained dialysate is determined. The mass transfer area coefficient of the patient's peritoneal membrane is then obtained as a function of the measured variables. Means are provided for conducting the method for each of the steps described.

18 Claims, 4 Drawing Sheets

APPARATUS AND METHOD FOR AUTOMATICALLY PERFORMING PERITONEAL EQUILIBRATION TESTS

BACKGROUND OF THE INVENTION

This invention relates to a method and apparatus for conducting automated peritoneal equilibration tests to prescribe a specific type of dialysis treatment for a patient. More particularly, the invention relates to an apparatus and method which employs the sensor system disclosed in U.S. application Ser. No. 07/959,922, filed Oct. 13, 1992 of Applicant, refiled May 9, 1994 as U.S. application Ser. No. 08/239,936, which disclosures are incorporated by reference herein. The sensor system of that application is used in an automated method and apparatus to automatically assess the diffusive and hydraulic transport properties of the peritoneal membrane of the patient.

In the field of dialysis, one form of dialysis treatment is known as peritoneal dialysis which can take different prescribed forms depending on a patient's clinical characteristics. Specifically, in peritoneal dialysis toxin removal occurs as a result of a diffusion gradient between the patient's bloodstream and the fluid in their peritoneal cavity. The rate of this removal is primarily dependent upon their "mass transfer area coefficient" (MTAC) of the given toxin. Fluid removal is osmotically induced by a difference in the glucose concentration between the peritoneal cavity and the bloodstream. Because glucose diffuses into the body, this gradient decreases so that the net transcapillary ultrafiltration rate is maximal at the beginning of the exchange, decreasing exponentially with time. Transcapillary ultrafiltration during exchanges using the same dialysis solution is dependent upon the MTACs of the various solutes and the overall hydraulic conductivity ($L_{PA}$) and lymphatic absorption rate ($Q_L$).

A significant cause of patient dropout from peritoneal dialysis is inadequate dialysis. Experience has shown that an appropriate regimen on one patient may not be sufficient for another. The reason for this is that each patient's peritoneal membrane has a unique mass transfer area coefficient affecting both clearance and ultrafiltration. Patients with high transport rates need short, frequent exchanges because of their tendency to reach equilibration much faster. Thus, nightly peritoneal dialysis usually can accomplish the needed dialysis for these types of patients. Alternatively, in some cases, daytime ambulatory peritoneal dialysis may be used.

Patients with high-average transport rates typically do well on standard-dose peritoneal dialysis in which 7.5 to 9.0 liters of dialysis solution is used per twenty-four hour period. Patients with low-average transport rates can be maintained on standard peritoneal dialysis if they have some residual renal function. Larger sized patients having this type of membrane permeability may require a higher dose peritoneal dialysis regimen. Finally, patients with low-transport rates may typically develop signs and symptoms of inadequate dialysis if maintained on standard peritoneal dialysis. As a result, a variation on the treatment employing high-dose peritoneal dialysis or hemodialysis itself may be required.

Since 1983, it has become common to systemically measure peritoneal transfer rates of urea, creatinine, glucose, protein, potassium and sodium as well as drained and residual volumes. This is done in what is known as the peritoneal equilibration test which has been performed over a four-hour dwell exchange, typically with 2 liters (L) of 2.5% glucose solution. The test has proved to be very useful for diagnostic, prognostic and dialysis-regimen-planning purposes.

Specifically, the standardized "peritoneal equilibration test" (PET) defines the peritoneal membrane clearance and ultrafiltration rates by measuring dialysate-to-plasma ratios of creatinine and glucose under specific conditions. Once the membrane permeability is identified, clinicians can more accurately select a peritoneal dialysis regimen to optimize dialysis based upon other parameters such as volume (or weight), fluid or food consumption, and urea generation rate. The results from the PET classify patients into the four basic groups as identified previously.

A standard PET is typically performed manually. An initial step involves infusing a patient with a known volume of exchange fluid. This volume is retained overnight by the patient and the overnight exchange is then drained, measured and a sample is taken. A known volume of fresh dialysate is then instilled into the peritoneal cavity of the patient. After installation, 200 ml of fluid are periodically drained (usually at 0, 120, and two-hundred forty minute intervals). A small sample of the fluid which is drained is then taken and the remaining fluid is immediately reinstilled into the peritoneal cavity. The urea, creatinine and glucose concentrations of the sample are measured. At the end of the dwell, "dwell" being the time the dialysis fluid is retained by the patient (approximately two-hundred forty minutes), all fluid is drained and the quantity of fluid drained is measured. A blood sample is then taken at mid-dwell (at about one-hundred twenty minutes). The urea, creatinine and glucose concentrations in the blood sample are measured.

From the solute concentration in the overnight exchange and the time-zero solute concentration, the residual volume is determined as $V_{Instill} \times C_0/(C_{ON}-C_O)$. The "mass transfer area coefficient" (MTAC) is determined as the slope of the regression of $\ln(1-C_D/C_P)$ versus time, times the negative of the average interperitoneal volume. The subscript "D" refers to the dialysate concentration while the subscript "P" refers to the plasma water concentration. On the basis of this calculated MTAC, it can be determined whether the patient is a high, high-average, low-average, or low transporter. From the overnight exchange volume and the PET drain volume, and the MTAC for glucose, the hydraulic conductivity $L_P$ and loss coefficient $Q_L$ of the membrane can be determined. From these parameters, ultrafiltration can then be predicted in a variety of therapies. Given these determinations, recommendations can then be made about the type of therapy a patient should receive as well as the therapy prescription, i.e., number of exchanges, volume of each exchange, etc. Estimations of the total weekly creatinine clearance can also then be obtained.

As can be appreciated from the PET, the method involved cumbersome manual manipulation of relatively large volumes of fluid. In addition, invasion into the body to obtain blood samples is also required, all of which take time and are resource intensive. In accordance with the invention, the PET is automated through the use of an existing sensor system as disclosed in the previously referenced co-pending application to result in a highly efficient and reproducible method and apparatus for conducting peritoneal equilibration tests for the purposes of determining appropriate therapy for a patient.

SUMMARY OF THE INVENTION

In accordance with one aspect of the invention, a method of automatically conducting a peritoneal equilibration test is provided. The method includes the step of removing a sample of previously infused overnight dwell fluid from a patient in an amount sufficient to determine the amount of a metabolite therein. The amount of metabolite in the sample is detected. The overnight dwell fluid is then drained from the patient and the weight of the drained overnight dwell fluid is determined. Thereafter a known weight of dialysate fluid of a known concentration of glucose is instilled into the patient. Samples are then periodically drawn from the dialysate fluid and the concentration of the metabolite in each sample is determined. The ratio of the metabolite concentration of the sample from the overnight dwell fluid to metabolite concentration for each of the periodically drawn samples of the dialysate fluid is determined. The patient is thereafter drained of the instilled dialysate fluid after a predetermined dwell time and the volume of the drained dialysate is also determined. The mass transfer area coefficient of the patient's peritoneal membrane can then be determined as a function of the known volume of dialysate infused, known volume of drained dialysate and the determined ratios of each of the periodically drawn samples.

In another aspect, the invention is directed to an apparatus for automatically conducting peritoneal equilibration tests. A device is provided for removing a sample of overnight dwell fluid from a patient for determining the amount of metabolite in the sample. A detector serves to detect the amount of metabolite in the sample. There is also provided a device for draining all overnight dwell fluid from the patient and for instilling a known weight of dialysate fluid of known glucose concentration into the patient. A scale serves to weigh the overnight dwell fluid drained from the patient. The device for removing a sample of overnight dwell fluid is also adapted for periodically drawing samples of instilled dialysate fluid. The detector for detecting the amount of metabolite in the sample from the overnight dwell also serves to detect the amount of metabolite in each periodically drawn sample. A measuring device serves to determine the volume of the instilled dialysate after withdrawal from the patient after a predetermined dwell time. A calculating device then serves to determine the mass transfer area coefficient of the patient's peritoneal membrane as a function of the determined volume of the dialysate infused, the known volume of the drained dialysate and the ratios of the determined metabolite in the sample of overnight dwell fluid to the determined metabolite in the drawn sample for each periodically drawn sample.

BRIEF DESCRIPTION OF THE DRAWINGS

Having generally described the invention, the same will become better understood from the following detailed discussion presented herein with reference to the appended drawings wherein.

DETAILED DISCUSSION

Figure 1:
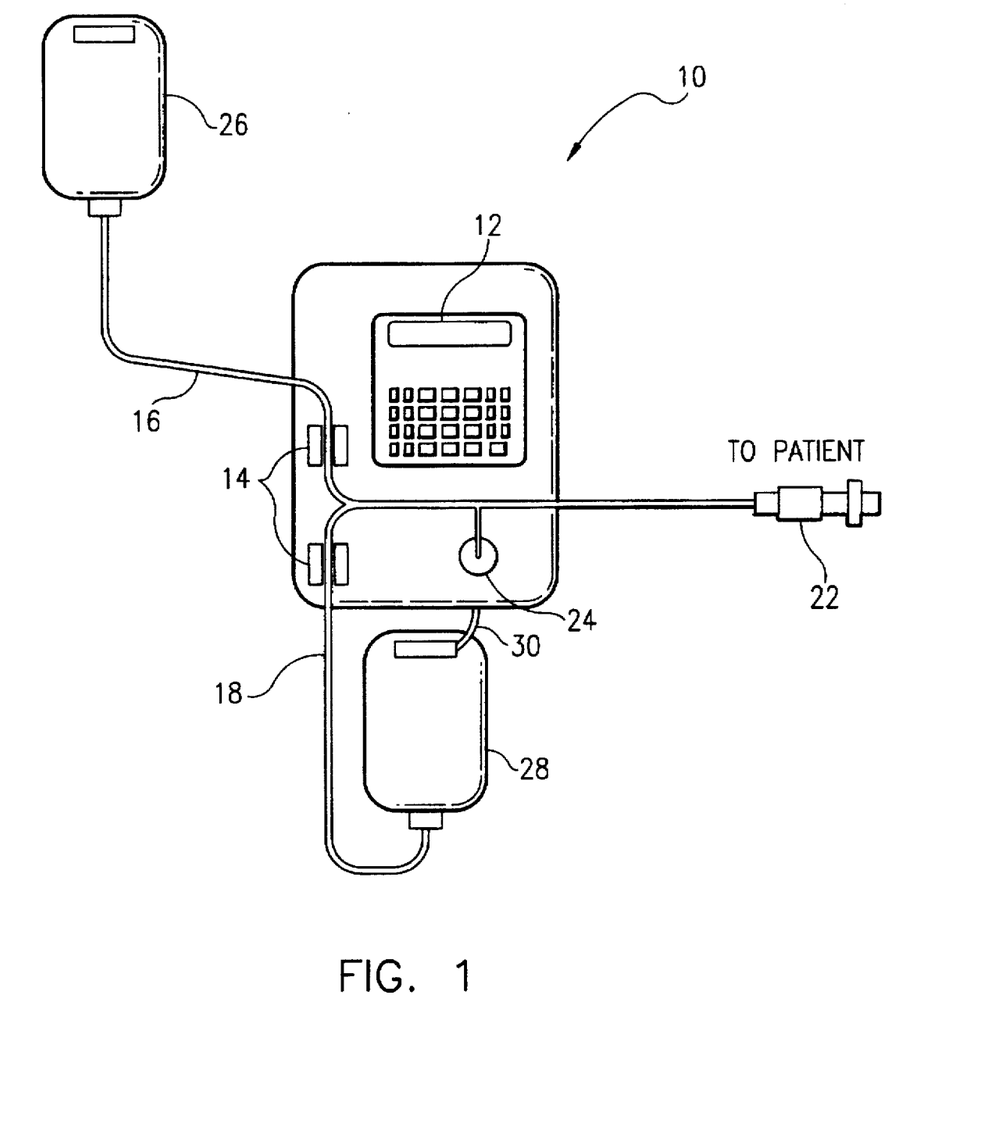
FIG. 1 is a schematic illustration of one embodiment of the device for conducting automated peritoneal equilibration testing in accordance with the invention.

One device for conducting the method in accordance with the invention is generally illustrated in FIG. 1 as reference numeral 10. The device 10 is essentially a module which directs or redirects a number of different flows through control of clamps 14 on tubing 16, 18 and 20 between a patient, a fresh dialysate source or bag 26 and drain dialysis bag 28 as well as through a filter and sample port 24 which leads to a sensor for detecting components in samples. The system is controlled through an input device such as a keypad 12 and is programmed in a conventional manner to direct the various flows. A connector 22 serves to connect the various flows to and from a patient for conducting the method in accordance with the invention.

Figure 2:
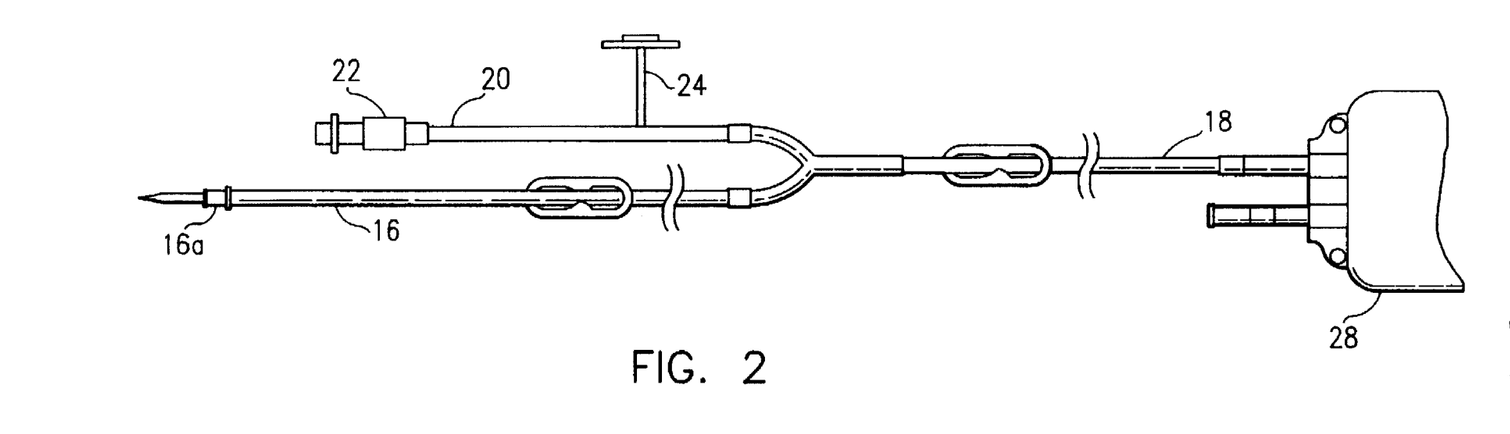
FIG. 2 is an enlarged view of the connecting arrangement employed in accordance with the invention to connect a patient to the device for conducting automatic testing in accordance with the invention and for connecting the patient to a fresh infusion of dialysate.

FIG. 2 shows more clearly a connecting arrangement of the type preferred for use in accordance with the invention, showing the various elements illustrated in FIG. 1 in greater detail and showing at the end of tubing 16 which connects to a fresh dialysate bag a dialysate bag connector 16a. It is noted that in conducting a method of the invention, it is important to weigh the various volumes flowed into and out of the patient. To this end, while no scale is shown relative to fresh dialysate bag 26, in FIG. 2 the drain bag 28 is connected to a scale 30 (FIG. 1) which serves to weigh the withdrawn fluid from a patient. Thus, the use of these various elements in conducting the method will become better appreciated from the discussion which follows.

Figure 3:
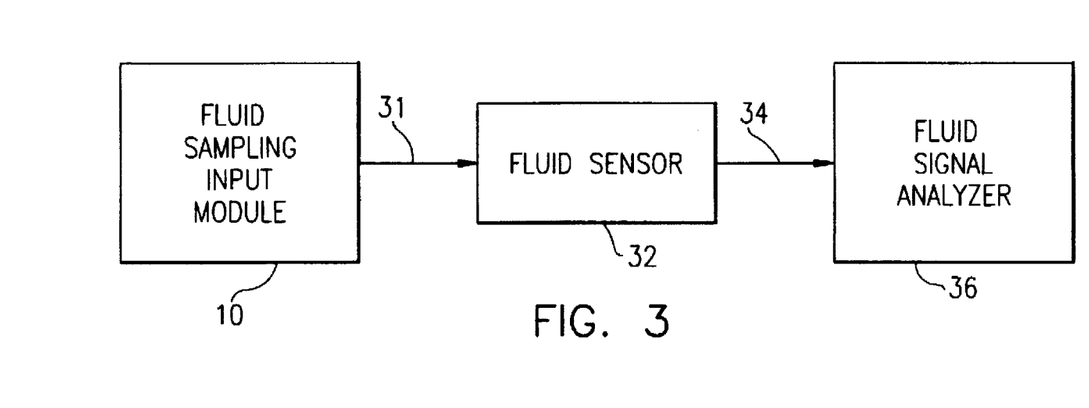
FIG. 3 is a block diagram showing the connection from the device for conducting automatic peritoneal testing to a fluid sensor and fluid signal analyzer for obtaining the results of the test.
Figure 4:
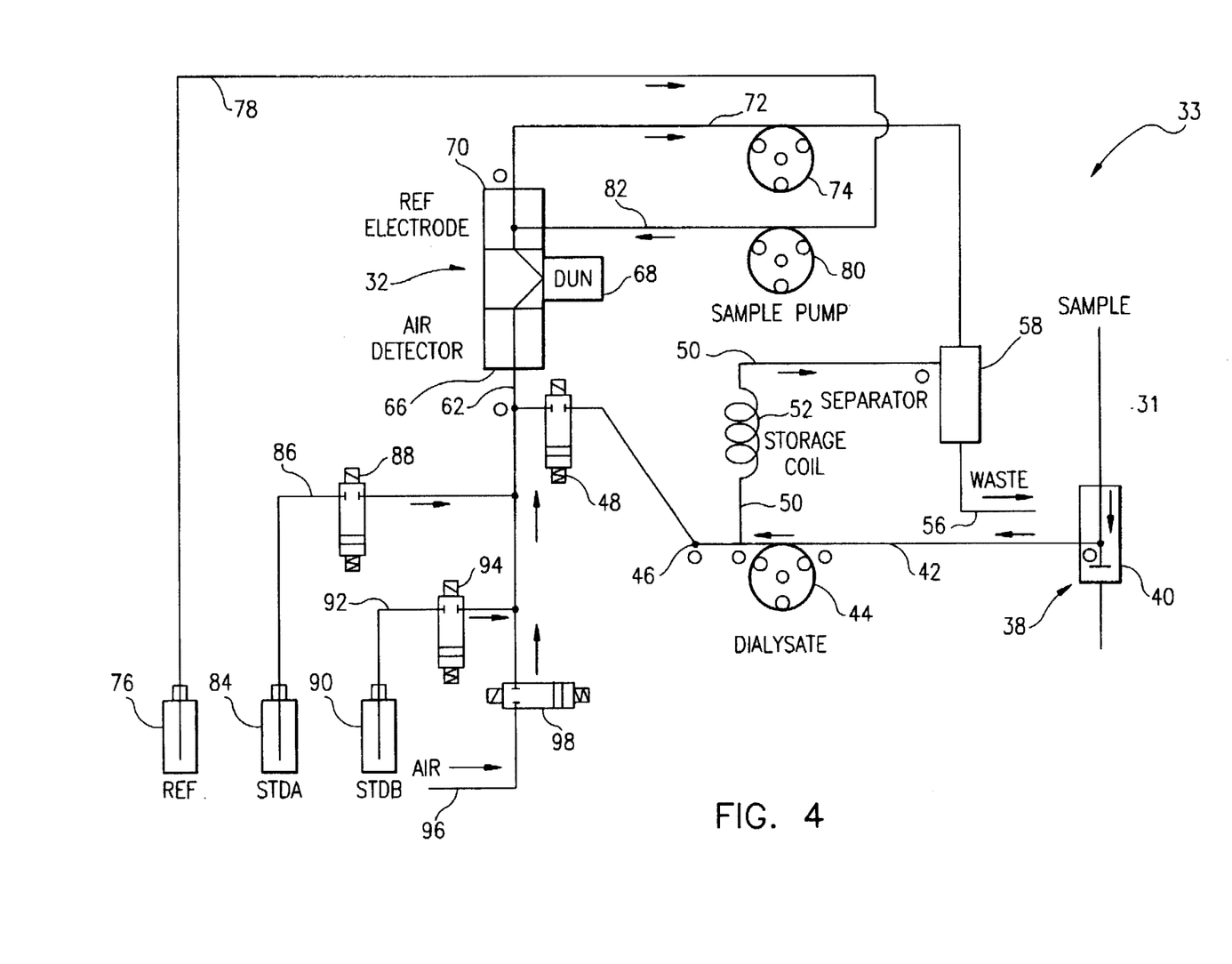
FIG. 4 is a more detailed view of a typical sensor system of the type employed in the invention to conduct the peritoneal equilibration testing.

In FIG. 3 there is shown a block diagram more clearly illustrating how the device for conducting the automatic peritoneal equilibration test 10 is connected through a sample line 31, which connects to filter and sample port 24 to a fluid sensor 32 (FIG. 3) more clearly illustrated in FIG. 4. Output from the fluid sensor 32 in terms of signals is provided to a fluid signal analyzer 36 which then calculates and provides to the clinician the appropriate values obtained from conducting the automated peritoneal equilibration test. Fluid signal analyzer can be part of module 10 of FIG. 1 as part of the hardware and programming thereof. In operation the sensor 32 is similar to the sensor disclosed in co-pending application Ser. No. 07/959,922, except that instead of detecting components in a dialysate flow from hemodialysis machine after exchange of metabolite with blood in the hemodialysis machine, the components are detected from samples taken from the peritoneal cavity of a patient by a sensor/system 33 as generally shown in FIG. 4.

The sensor 32 is minimally a urea sensor. In the preferred embodiment, however, both urea and creatinine sensors will be included in the device. There are various approaches to urea and creatinine sensing and virtually any sensor can be used for this purpose. The invention, therefore, is not specific to any particular type of sensor. However, urea and creatinine are significant, identifiable metabolites which can be used as markers of toxin removal. Other constituents are, for example, uric acid, phosphate, calcium, sodium, potassium, glucose, and beta 2 microglobulin, among others.

In use in the invention, the system 33 is connected to a sample through sample line 31 and includes the urea sensor 32 described previously.

In operation, the system 33 can sample dialysate from the peritoneal cavity by having clamps 14 shut both with respect to the drain bag 28 as well as the fresh dialysate bag 26 (FIG. 1) and activating a self-occluding peristaltic or roller pump 44 (FIG. 4). The system 33 taps into the sample line 31 through a junction 40 of sample port 38 connected to filter and port 24 (FIG. 1) through line 31 which is itself coupled to sampling line 42 (FIGS. 3 and 4). The line 42 is coupled to a junction 46 into a normally closed valve 48. The junction 46 is also coupled to a line 50 which includes a storage coil 52. The storage coil 52 is first filled with the dialysate sample, with excess dialysate effluent, if any, continuing through line 50 to separator 58. The separator 58 includes an air gap which prevents a backup of dialysate sample effluent and also prevents an electrical short through line 56.

Once storage coil 52 is filed, the pump 44 is stopped, which closes the line 42 from the junction 38. The valve 48 is then opened allowing the sample dialysate to flow through the valve 48 into a line 62 and then to and past the urea sensor 32. The sample dialysate is caused to flow by a sample pump 74, which is coupled between the urea sensor 32 and the discharge separator 58 by a line 72.

Before the sample dialysate is pumped through the urea sensor 32, a reference fluid from a source 76 is pumped into the urea sensor 32 through a line 78 and second pump 80 through line 82. The second pump 80 preferably can be a second roller head on the pump 74, but could also be a second pump coupled to operate at the same time as the pump 74.

As shown in more detail in U.S. Pat. No. 4,686,479, the urea sensor 32 can be the type which includes an air detector 66 to determine if the sample dialysate is present in the urea sensor 32. The sensor 32 employs an electrode 68 with a membrane (not illustrated) which is specific to ammonium. The electrode 68 senses "dialysate urea nitrogen" (DUN) which is compared to a reference electrode 70. The signal generated by the sensor 32 then is coupled to signal analyzer 36 (FIG. 3), which makes a number of calculations to provide the results of the peritoneal equilibration test as will be described in more detail hereafter.

Although not shown, sensor 32 can have additional sensors such as a creatinine sensor and a phosphate arranged in series therewith. Alternatively, sensor 32 can itself be a creatinine or phosphate sensor instead of a urea sensor. Thus, while the invention is described with respect to urea, as can be appreciated, it may be practiced by measuring other metabolites. The sensors themselves are preferably ion specific sensors which have a high and low concentration standard which is read by the sensor to generate a concentration-voltage curve. The unknown is then measured and its voltage is read off of this curve to yield its concentration. When more than one sensor is used, i.e., two, they are placed in series, and the known concentration of metabolites are added to the standard particular to the respective sensor. Thus, in the case of two sensors, there are only two standards and all metabolites are measured simultaneously. Alternative arrangements can involve parallel placement of sensors, but this requires reading of metabolites individually, and is not as efficient.

At the beginning of the test with a patient, and periodically as desired, both a low-reference and a high-reference standard are run on the system 33 to calibrate the system 33. To calibrate the system 33 with the low standard, the valve 48 remains closed and a valve 88 is opened to allow the pump 74 to draw in the low-standard fluid from a source 84 through a line 86. The urea sensor 32 measures the low standard, which is compared to an expected range of values to ensure that the urea sensor 32 is calibrated correctly. The low standard also can be utilized to test the integrity of the system 33 during testing.

A similar operation is performed with a high-reference standard. To run a high-standard test, all the valves are closed, except for a high-standard valve 94. The open valve 94 allows the pump 74 to draw a high-standard fluid from a source 90 through a line 92. The high-standard fluid is measured in the urea sensor 32 and compared to an expected range of values to ensure that the urea sensor is also operating correctly at the high-standard range.

At the end of the low-standard cycle testing, the system 33 closes the valves 48, 88 and 94 and opens an air valve 98 for a period of time which allows the second pump 80 to draw air into a line 96 through the valve 98, the urea sensor 32 and out the discharge line 56. The air segment between each fluid segment helps ensure that the urea sensor 32 and the lines 62 and 72 are clean and empty of any substantial mount of residual fluid.

In accordance with the method of the invention, a patient is instructed not to perform a peritoneal exchange past midnight the day before being tested so that at least eight hours elapse prior to the automated peritoneal equilibration test. The patient is also instructed to collect their urine for twenty-four hours, if they have any, and all of their dialysate. When the test is to be conducted, several patient inputs, as listed below, are requested by the device 10 which can be input through the keyboard 12. The inputs are as follows:

| INPUT | | ABBREVIATION |
|---|---|---|
| a. | Height. | H |
| b. | Weight. | W |
| c. | Sex. | S |
| d. | Name & I.D. #. | |
| e. | % Dextrose for test. | CGT |
| f. | Amount of fluid to be infused for test. | VTI |
| g. | % Dextrose for overnight dwell. | CGN |
| h. | Amount of fluid infused for overnight dwell. | VNI |
| i. | Urine volume over 24 hours. | VU |
| j. | Number of exchanges in last 24 hours. | $N_x$ |
| k. | Volume infused each exchange. | $VI_x$ |
| l. | Volume drained each exchange. | $VD_x$ |
| m. | Glucose concentration of exchange. | $CG_x$ |
| n. | Time of each exchange. | $T_x$ |

As noted, the automatic peritoneal equilibration testing device includes a keypad 12 with a one-line display so that the above inputs can be abbreviated as noted.

Prior to starting the test exchange and connecting the patient, the automatic peritoneal equilibration testing device is allowed to sample some of the patient's urine through filter and sample port 24 to the system 33. A similar amount of dialysate from each of the bags collected during the preceding twenty-four hours is also collected. These yield the values "CU" (the concentration of urea in the urine) and "$CD_x$" (the concentration of urea in each exchange). From this and input "i" which refers to the urine volume over twenty-four hours, the residual clearance can be calculated as: $K_R = V_U C_U/(C_{ON} * 1440)$ ($C_{ON}$ is determined as described hereafter and refers to urea concentration in a sample from the overnight dwell in a patient). In a similar fashion, the urea generation rate "g" can also be calculated as $\Sigma (V_{Dx} C_{Dx})/1440$ (yielding a value in mg/min.), as well as the total clearance for the twenty-four hour period $\Sigma (V_{Dx} C_{Dx})/(C_{ON}/1000)$ yielding a value in liters.

After obtaining the urea concentration in the urine, the patient is then connected through appropriate sterile procedures to the line set shown in FIG. 2. A pre-attached empty drain bag 28 is shown connected through tubing 20 which splits into two sets of tubes at a "T" connection through a small diameter tube which is actually the filter and sample port 24 which connects to the device 10. Connector 22 is connected to the patient and connector 16a is the spike connector for connection to a fresh dialysate bag 26. The filter of filter and sample port 24 is typically a 0.22 μ or 0.471 μ sterile filter which is changed for each patient test.

The device 10 signals that draining from the patient should begin and the nurse or clinician presses an appropriate key on the keyboard 12 to cause the drain bag clamp 14 connected to line 18 to begin draining the patient by gravity and presses a button on the keyboard 12 indicating that draining has started. After one minute the device 10 takes a sample from the "T" connection shown in FIG. 2 as filter and sample port 24. The urea concentration is measured in this sample through the operation of the device, as described with reference to FIGS. 3 and 4, to result in a urea concentration ($C_{ON}$) for the sample from the overnight dwell. Draining continues for a period of twenty minutes or until the patient begins to feel it "pull." A button is pushed on the keyboard 12 of the device 10 indicating that draining has stopped. The drain time for the overnight dwell is then calculated or determined by the device 10 and is identified as (TN). The amount of drain fluid (VNO) is the weighed by scale 30.

Infusion of fresh dialysate from fresh dialysate bag 26 now begins through line 16 and open clamp 14 corresponding to line 16 with clamp 14 corresponding to line 18 being closed. The nurse pushes a button operating the clamps 14 as described and another button on the keyboard 12 is pushed to indicate the infusion has started. After infusion is finished, another button is pushed. This allows the device 10 to calculate the infusion time (TI). While the connections of FIG. 2 could be used alone with a separate input module and manual opening and closing of clamps as illustrated in FIG. 2, and with weighing done on an external scale and values being entered manually by different keypads, in the preferred embodiment as shown in FIG. 1, solenoid clamps 14 are used to open and close lines to the drain bag 28 and fresh dialysate bag 26. Weighing is done preferably by using the integrated scale 30 shown in FIG. 1.

Once the infusion is completed, this is taken to be the "zero" or "reference time." The device 10 then draws a sample through its sample port and filter 24 into system 33 and the concentration of urea in this sample is determined by system 33 and fluid signal analyzer 36 of module 10 as ($C_0$). Samples are then subsequently drawn at equally spaced time intervals and the urea concentration is measured ($C_{Di}$) until a preset dwell time is reached, typically about ninety minutes. Each sample including the zero-time sample and the overnight dwell sample is of a size of typically 20 ml of fluid which is subsequently thrown away or discarded through waste line 56. This amount of fluid is required to obtain a representative sample washing out the dead space in the line set and patient's catheter.

Figure 5:
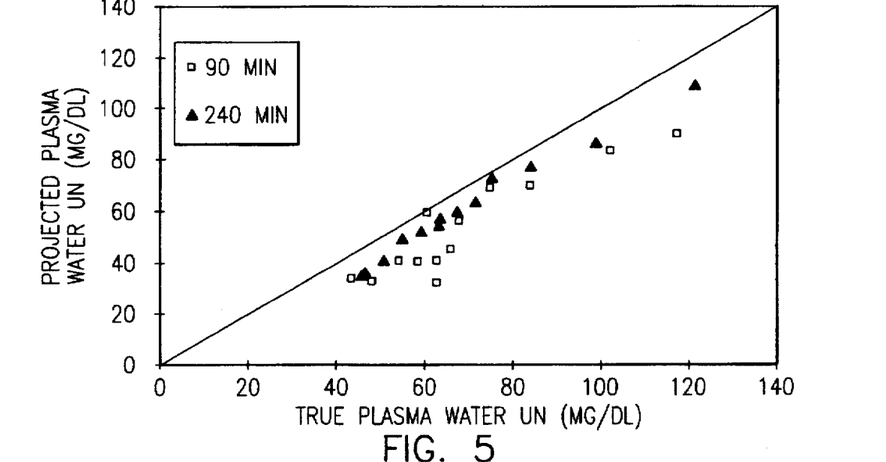
FIG. 5 is a graph showing the correlation of projected plasma water urea nitrogen concentration to actual plasma water urea nitrogen concentrations with ninety and two-hundred forty minutes of data.

$C_{ON}$ is used as an estimate of the plasma/water concentration which is used subsequently in predicting the mass transfer area coefficient. It is conceivable that $C_{ON}$ may be in a range which is not easily measured, or some other difficulty may interfere with an accurate determination of $C_{ON}$ (e.g., the patient may be an extremely poor transporter so $C_{ON}$ is not fully equilibrated with the blood). Under these circumstances an estimate of $C_{ON}$ may be determined from the transient dialysate concentrations ("Di") as follows:

Using a Levenberg-Marquardt nonlinear fitting method, the function $C_{Di} = C_{DO} + (P - C_{DO})[1 - e^{\gamma(t-t_o)}]$ is fit knowing a multiplicity of concentrations $C_{Di}$ at times "t". This is a two-parameter fit where $C_{DO}$ is taken to be the concentration $C_{Di}$ at time "to" shortly after zero time. Thus, only "γ" and "P" are independent parameters. "P" gives a reasonable approximation to the plasma/water concentration. In FIG. 5, for eleven patients, the correlation coefficient "r" was 0.922 for ninety (90) minutes worth of data, and 0.986 for two-hundred forty (240) minutes worth of data. Since "P" is consistently below the true plasma/water concentration, a correction can be made so that:

$$\text{True plasma/water concentration} = mP + b \sim C_{ON};$$

where "m" and "b" are empirically determined from a database of peritoneal equilibration test (PET) data which has been obtained from measurements conducted on randomly selected set of patients. As well known to those of ordinary skill in the art, if there is not an accurate curve fit, the values "m" and "b" provide "correction factor" in a standard manner as discussed hereafter. For the eleven patients in FIG. 5: m=0.62 and b=9.5, when projecting from ninety minutes worth of data, or m=0.98 and b=4.4, when projecting with two-hundred forty minutes worth of data. It should be appreciated that more comprehensive data sets will provide similar but slightly different constants. $C_{ON}$ determined in this way can provide a check on the measured $C_{ON}$, or can be used in lieu of an actual overnight concentration.

Figure 6:
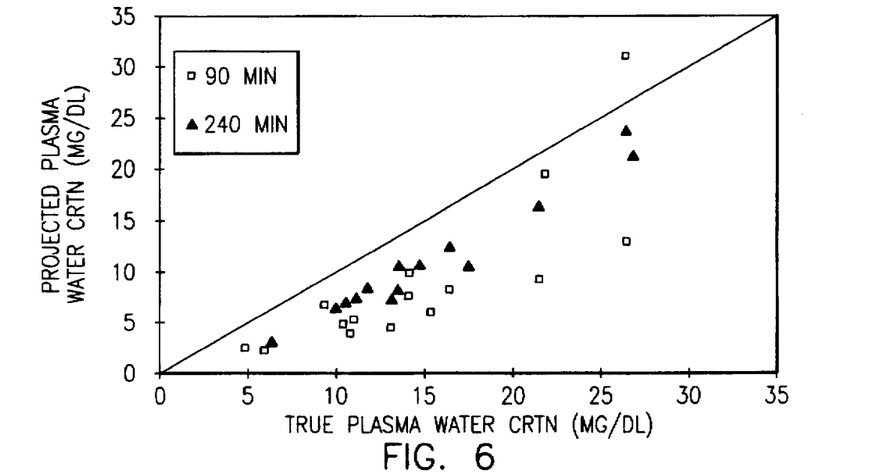
FIG. 6 is a graph showing the correlation of projected plasma water creatinine concentrations to actual plasma water creatinine concentrations with ninety and two-hundred forty minutes of data.
Figure 7:
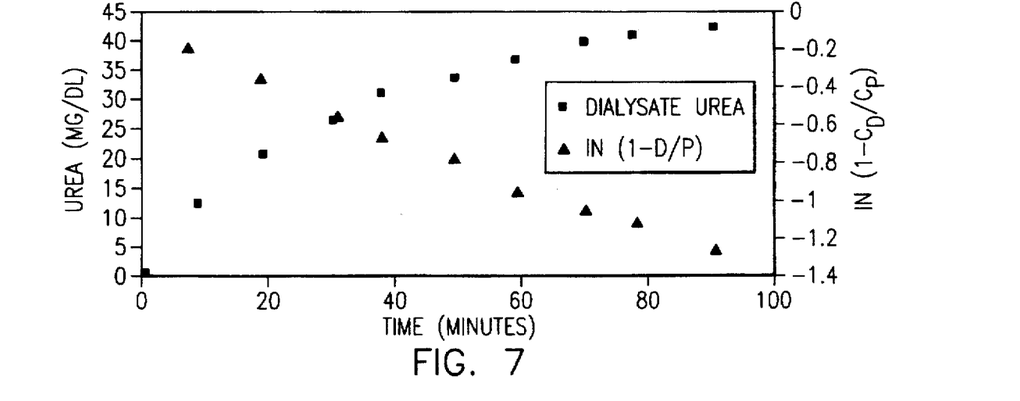
FIG. 7 is a graph of the dialysate urea concentration as a function of time during a typical test exchange (left "y" axis) and the natural log of one minus the dialysate urea concentration divided by the plasma/water concentration (right "y" axis).

FIG. 6 shows a similar graph for creatinine. The "r" values between the projected and actual plasma water values are 0.80 using the 90 minute data, and 0.97 using the 240 minute data. Appropriate values for "m" and "b" for creatinine are 0.61 and 9.56, when using 90 minutes of data, or 1.0 and 4.4 when using 240 minutes of data. The resulting projected plasma water concentration can then be used in lieu of $C_{ON}$ in obtaining the creatinine plasma water concentration as described below.

In accordance with the values obtained, the residual volume is then calculated as:

$$RV = \frac{VTI * C_0}{(C_{ON} - C_0)}$$

If from this calculation RV is determined to be greater than 0.333*VTI then RV will be set at a value of $V_{Avg\ Resid}$ which is typically 260.

At the end of the dwell time, the patient is drained into the drain bag 28 which is then weighed. The volume of the drain bag is given as VT0.

The mass transfer area coefficient for urea for the peritoneal membrane is then calculated as follows:

a. $y_i = \ln(1.0 - C_{Di}/C_{ON})$ $x_i = t_i$ where i=0..n b. The slope and y intercept are determined by:

$$\text{slope} = \frac{S^*S_{xy} - S_xS_y}{\Delta}$$

$$\text{intercept} = \frac{S_{xx}^*S_y - S_xS_{xy}}{\Delta}$$

where $$S = 1 \quad S_x = \sum_{i=1}^{n} x_i \quad S_y = \sum_{i=1}^{n} y_i$$

$$S_{xx} = \sum_{i=1}^{n} x_i^2 \quad S_{xy} = \sum_{i=1}^{n} x_iy_i \quad \Delta = S^*S_{xx} - (S_x)^2$$

then c. $MTAC_{urea} = \text{slope}^*V_{AV}$ where $V_{AV} = (VTI+VTO)/2+RV$ d. the four hour $C_D/C_P$ is extrapolated from the MTAC as $Y_{240} = MTAC/V_{AV} * (240)+\text{intercept}$ so $(C_D/C_P)_{240} = -(\exp(Y_{240})-1.0)$ The ratio is then displayed to the clinician. The patient is, based on this ratio, classified as "high," "high-average," "low-average" or "low" depending upon whether the two-hundred forty minute $(C_D/C_P)_{240}$ is greater than $l_1$, between $l_1$ and $l_2$, between $l_2$ and $l_3$, or less than $l_3$. The message is then displayed to the clinician. Typical values obtained for $l_1$, $l_2$ and $l_3$ are respectively 0.911, 0.846 and 0.781. These values represent the mean $(C_D/C_P)_{240}$ ratio ($l_2$), plus one standard deviation ($l_1$) and minus one standard deviation ($l_3$) determined from a cross-section of CAPD patients. When a creatinine sensor is installed in the device, a process similar to that described above is performed. The values for $l_1$, $l_2$ and $l_3$ are then different, typically 0.75, 0.60 and 0.39, respectively. From the mass transfer area coefficient for urea, the mass transfer area coefficient for creatinine (when a creatinine sensor is not included in the device) and glucose can be respectively calculated from a molecular weight relationship as follows:

$$MTAC_{creatinine} = MTAC_{urea} \frac{(60.06/113.12)^{0.333}(60.06)^{a_1}}{(113.12)^{a_1}}$$

where $$MTAC_{glucose} = MTAC_{urea} \frac{(60.06/113.12)^{0.333}(60.06)^{a_2}}{(180.16)^{a_2}}$$

where $a_1$ and $a_2$ are empirically determined constants close to 0.5.

It can be appreciated that $MTAC_{creatinine}$ and $MTAC_{glucose}$ can be determined from $MTAC_{urea}$ by formulae having a variety of foci since the nature of this relationship is primarily empirical. Those given here are for illustrative purposes. Furthermore, it can be appreciated that $MTAC_{urea}$ need not be explicitly calculated, but that since $\text{intercept}_{urea} \sim 1$, a relationship can be devised between $\text{slope}_{urea}$, $\text{slope}_{creatinine}$ and $\text{slope}_{glucose}$. Therefore, using the MTAC, or simply the slope value for creatinine and glucose, then the $(C_D/C_P)_{240}$ ratios for creatinine and glucose can be determined as determined above for urea. These ratios are then displayed to the clinician. Thereafter an ultrafiltration calculation is conducted. In order to estimate typical fluid removal from the patient, two parameters known as the hydraulic conductivity $L_{PA}$ and $Q_{Lo}$ are calculated from the data entered for the twenty-four hour collection period using the following equations:

$$VD = VI \left\{ 1 + 1.5 L_{PA} \sum_{i=1}^{m} K_i^{-1} \sigma_i(C_{D,i} - C_{B,i})(1 - e^{K_i t/VI}) \right\}^{\frac{2}{3}} e^{-Q_L t/VI}$$

where $K_i = MTAC_i - 1.5$ QL $VI_x$ = Infusion volume plus residual volume in liters. One value for each exchange.

$VD_x$ = Drain volume plus residual volume in liters. One value for each exchange.

$C_{B,i}$ = Blood concentration of urea, creatinine and glucose in mmol/liter. (Blood concentration of urea is the ON dwell concentration, blood concentration of creatinine and/or glucose are user input and/or "standard." It is assumed that for the most part, the patient's blood concentration is constant. Standard creatinine and glucose concentrations can be taken to be 12.5 mg/dl. [It is presumed the blood concentrations are the same for each exchange.]

$C_{D,i,X}$ = Initial dialysate concentration in mmol/liter. (For creatinine and urea these are zero.) Note that each infusion may have a different glucose concentration.

$t_x$ = Dwell time for each exchange.

It should be noted that the sum $i=1$ to $m$ is over the solutes urea, creatinine and glucose. Thus, $K_i$ uses the three-mass transfer area concentration values for urea, creatinine and glucose determined earlier. The parameter $\sigma_i$ has values for each of these three solutes close to 1.0.

Since the equation is nonlinear, the following routine is used to estimate the two parameters. This procedure uses the infusion and drain volumes from each of the exchanges during the twenty-four hour collection period. The correct pair of values of $L_{PA}$ and $Q_{Lo}$ will result in a minimum difference between measured and calculated drain volume as shown below in step "d":

a. Start with values of $Q_L = 0.1$. With the drain volume, time period and concentration in the drain bag for each exchange, calculate $L_{PA,i}$ for each exchange.

b. Find the arithmetic average of the $L_{PA}$'S for the exchanges.

c. Using the average $L_{PA}$ and assumed $Q_L$, calculate the drain volume for each exchange.

d. Calculate the minimization function as $$M = \sum_{1}^{n} |VD_{measured} - VD_{calculated}|_i^2$$

e. Repeat "a" through "d" incrementing $Q_L$ by $\Delta Q_L$ until $Q_L = 3.0$ and the minimum "M" is obtained.

f. If the value of $L_{PA}$ corresponding to the minimum "M" is negative or zero, then set $Q_L = 1.5$ and recalculate $L_{PA}$ using only the exchanges of short duration (less then six hours) and indicate to the user that $L_{PA}$ may be inaccurate.

While the invention has been described with specific emphasis on urea and a second emphasis on creatinine as the metabolites measured, it will be appreciated that measurement of a number of different metabolites, with appropriate adjustment of the calculations in a manner which will be apparent to those of ordinary skill in the art, can be used to practice the invention. For instance, a glucose sensor can be used in addition to the urea and creatinine sensor to conduct a dual analysis of each dialysate sample.

Having thus described the invention in detail, the same will become better understood from the appended claims which define the invention in a non-limiting manner.

What is claimed is:

1. A method of automatically conducting peritoneal equilibration tests, comprising:

removing a sample of overnight dwell fluid through a line from a patient in an amount sufficient to determine the concentration of a metabolite therein, said line being connected to control means for controlling removal of said sample;

detecting the concentration of at least one metabolite in said sample of overnight dwell fluid with detecting means for detecting said concentration, said detecting means being connected to said line and associated with said control means;

draining all overnight dwell fluid from a patient through said line under control of said control means to result in a drained overnight dwell fluid, and determining the weight of said drained overnight dwell fluid with weight means for weighing, associated with said control means;

instilling a known weight of dialysate fluid into a patient through said line under control of said control means;

periodically drawing samples of said dialysate fluid, under control of said control means, to result in periodically drawn samples of dialysate fluid, and determining the concentration of the metabolite in each one of said periodically drawn samples of dialysate fluid, with said detecting means;

determining the ratio of said metabolite concentration detected for each one of said periodically drawn samples of dialysate fluid to the metabolite concentration detected of said sample of overnight dwell fluid or other estimate of plasma water concentration, said determination being done by said control means;

draining the patient of said instilled dialysate fluid after a predetermined dwell time under control of said control means, and determining the volume of said drained dialysate fluid; and determining the mass transfer area coefficient of the patient's peritoneal membrane as a function of said known volume of dialysate fluid infused, known volume of drained dialysate fluid and the determined ratios of said metabolite concentration for each of said periodically drawn samples of dialysate fluid, to the metabolite concentration of said sample of overnight dwell fluid or other estimate of plasma water concentration.

2. A method as in claim 1 wherein said plasma water concentration is $C_{On}$ determined from said periodically drawn samples of dialysate fluid by performing a curve fit to a one minus exponential function of the form $C_{Do}+(P-C_{Do})[1-e^{\gamma(t-t_0)}]$, where $C_{Do}$ is a first plasma water concentration at a time "$t_0$", "t" is the time at which respective periodically drawn samples are drawn, "P" is a number empirically correlated to the plasma water concentration, and "$\gamma$" is an independent parameter of a Levenberg-Marguardt nonlinear fitting method, so that $C_{ON}=mP+b$, where "m" and "b" are determined from a database of peritoneal equilibration test (PET) data.

3. A method as in claim 2 wherein said metabolite measured further comprises one of creatinine and phosphate.

4. A method as in claim 3 further comprising measuring a plurality of different metabolites.

5. A method as in claim 1 wherein said metabolite measured is urea or creatinine.

6. A method as in claim 1 wherein said ratios of concentration of metabolite in the overnight sample to concentration for any periodically drawn sample of dialysate fluid is used to project the ratio at any given time based on the slope of in $(1-C_{Di}/C_{ON})$ versus $t_i$ which is assumed to be a straight line, where $t_i$ is the time at which any sample is withdrawn, $C_{Di}$ is the concentration of metabolite for any periodically drawn sample of dialysate fluid, so that said ratio at time t is $-(\exp(f(\text{slope}_{urea})t+\text{intercept})-1.0)$, where f (slope) is an empirically derived function of said slope.

7. A method as in claim 6 wherein said metabolite measured is urea or creatinine.

8. A method as in claim 1 wherein the mass transfer area coefficient calculated is compared to a set of standard values to determine the degree of transport of a patient's peritoneal membrane.

9. A method as in claim 1 wherein said plasma water concentration is $C_{ON}$ determined from said periodically drawn samples of dialysate fluid by performing a curve fit to a one minus exponential function of the form $C_{Do}+(P-CD_{Do})[1-e^{\gamma(t-t_0)}]$, where $C_{Do}$ is a first plasma water concentration at a time "$t_0$", "t" is the time at which respective periodically drawn samples are drawn, "P" is a number empirically correlated to the plasma water concentration, and "$\gamma$" is an independent parameter determined from a nonlinear least squares fitting method, so that $C_{On}=mP+b$, where "m" and "b" are determined from a database of peritoneal equilibration test (PET) data.

10. An apparatus for automatically conducting peritoneal equilibration tests, comprising:

means for removing a sample of overnight dwell fluid from a patient for determining the amount of a metabolite in said sample;

means for detecting the concentration of metabolite in said sample;

means for draining all overnight dwell fluid from a patient and for instilling a known weight of dialysate fluid into said patient;

means for weighing said overnight dwell fluid drained from said patient;

said means for removing a sample of overnight dwell fluid being also for periodically drawing samples of instilled dialysate fluid and said means for detecting being for detecting the amount of metabolite in each periodically drawn sample;

means for determining the volume of said instilled dialysate after withdrawal from said patient after a predetermined dwell time; and calculating means for determining the mass transfer area coefficient of the patient's peritoneal membrane as a function of the determined volume of dialysate infused, known volume of drained dialysate and the ratios of the determined metabolite for each periodically drawn sample to the determined metabolite in the sample of overnight dwell fluid or other estimate of the plasma water concentration.

11. An apparatus as in claim 10 further comprising means for determining the plasma water concentration from periodically drawn samples of dialysate fluid by performing a curve fit to a one minus exponential function of the form $C_{Do}+(P-C_{Do})[1-e^{\gamma(t-t_0)}]$, where $C_{Do}$ is a first plasma water concentration at time "$t_0$", "t" is the time at which respective periodically drawn samples are drawn, "P" is a number empirically correlated to the plasma water concentration, and "$\gamma$" is an independent parameter of a Levenberg-Marguardt nonlinear fitting method, for having $C_{ON}=mP+b$, where "m" and "b" are determined from a database of peritoneal equilibration test (PET) data.

12. An apparatus as in claim 11 further comprising means for measuring at least one of creatinine and phosphate.

13. An apparatus as in claim 12 wherein said means for measuring further comprises means for measuring a plurality of different metabolites.

14. An apparatus as in claim 10 wherein said means for detecting is for detecting the concentration of urea or creatinine.

15. An apparatus as in claim 10 further comprising means for projecting the ratio of concentration of metabolite in the overnight sample to concentration of any periodically drawn sample at any time based on a calculation of ln $(1-C_{Di}/C_{ON})$ versus $t_i$ which is assumed to be a straight line, where $t_i$ is the time at which any sample is withdrawn, $C_{Di}$ is the concentration of any referenced sample withdrawn at different times $t_i$ and $C_{ON}$ is the overnight dwell sample concentration.

16. An apparatus as in claim 15 wherein said means for detecting is for detecting the concentration of urea or creatinine.

17. An apparatus as in claim 10 further comprising comparing means for comparing the mass transfer area coefficient calculated to a set of stored standard values to determine the degree of area and permeability of a patient's peritoneal membrane.

18. An apparatus as in claim 10 further comprising means for determining the plasma water concentration from periodically drawn samples of dialysate fluid by performing a curve fit to a one minus exponential function of the form $C_{Do}+(P-C_{Do})[1-e^{\gamma(t-to)}]$, where $C_{Do}$ is a first plasma water concentration at time "$t_0$", "t" is the time at which respective periodically drawn samples are drawn, "P" is a number empirically correlated to the plasma water concentration, and "$\gamma$" is an independent parameter determined from a nonlinear least squares fitting method, so that $C_{ON}=mP+b$, where "m" and "b" are determined from a database of peritoneal equilibration test (PET) data.

* * * * *

UNITED STATES PATENT AND TRADEMARK OFFICE
CERTIFICATE OF CORRECTION

PATENT NO. : 5,670,057

DATED : September 23, 1997

INVENTOR(S) : Chi Chen, et al.

It is certified that error appears in the above-identified patent and that said Letters Patent is hereby corrected as shown below:

Column 5, Line 24: delete "filed" and insert --filled--

Column 6, Line 26: delete "mount" and insert --amount--

Column 7, Line 21: delete "0.471" and insert --0.47--

Column 8, Line 26: delete "True plasma/water concentration=mP+b~$C_{ON}$;" and insert
--True plasma/water concentration=mP+b$\approx C_{ON}$;--

Column 9, Line 29: delete "($1_2$)" and insert --($\ell_2$)--

Column 9, Line 30: delete "($1_1$)" and insert --($\ell_1$)--

Column 9, Line 30: delete "($1_3$)" and insert --($\ell_3$)--

Column 9, Line 33: delete "$1_1$, $1_2$" and insert --$\ell_1$, $\ell_2$--

Column 9, Line 34: delete "$1_3$" and insert --$\ell_3$--

UNITED STATES PATENT AND TRADEMARK OFFICE
CERTIFICATE OF CORRECTION

PATENT NO. : 5,670,057
DATED : September 23, 1997
INVENTOR(S) : Chi Chen, et al.

It is certified that error appears in the above-identified patent and that said Letters Patent is hereby corrected as shown below:

Column 9, Line 56: delete "intercept$_{urea}$~1," and insert --intercept$_{urea} \approx 1$,--

Column 12, Line 5: delete "in" and insert --$\ell n$--

Column 13, Line 2: delete "peritoneal equilibration test (PET) data." and insert
--equilibration test (PET) data, and a database of PET data for providing said "m" and "b" values.--

Signed and Sealed this

Thirtieth Day of June, 1998

Attest:

BRUCE LEHMAN

Attesting Officer

Commissioner of Patents and Trademarks